United States Patent
Hirose et al.

(10) Patent No.: US 10,633,532 B2
(45) Date of Patent: Apr. 28, 2020

(54) RESIN COMPOSITION CONTAINING ISOBUTYLENE-BASED COPOLYMER, AND MOLDED OBJECT

(71) Applicant: KURARAY CO., LTD., Kurashiki-shi (JP)

(72) Inventors: Wataru Hirose, Kurashiki (JP); Takeyuki Igarashi, Okayama (JP)

(73) Assignee: KURARAY CO., LTD., Kurashiki-shi (JP)

( * ) Notice: Subject to any disclaimer, the term of this patent is extended or adjusted under 35 U.S.C. 154(b) by 16 days.

(21) Appl. No.: 15/773,242

(22) PCT Filed: Nov. 2, 2016

(86) PCT No.: PCT/JP2016/082682
§ 371 (c)(1),
(2) Date: May 3, 2018

(87) PCT Pub. No.: WO2017/078103
PCT Pub. Date: May 11, 2017

(65) Prior Publication Data
US 2018/0319972 A1    Nov. 8, 2018

(30) Foreign Application Priority Data

Nov. 4, 2015  (JP) ................ 2015-217060

(51) Int. Cl.
| | |
|---|---|
| *C08L 53/00* | (2006.01) |
| *C08L 29/04* | (2006.01) |
| *C08L 23/28* | (2006.01) |
| *C08K 3/26* | (2006.01) |
| *A61L 31/12* | (2006.01) |
| *C08L 23/22* | (2006.01) |
| *A61J 1/10* | (2006.01) |
| *C08L 23/08* | (2006.01) |
| *C08L 53/02* | (2006.01) |
| *C08F 297/00* | (2006.01) |

(52) U.S. Cl.
CPC ............... *C08L 53/00* (2013.01); *A61J 1/10* (2013.01); *A61L 31/12* (2013.01); *C08F 297/00* (2013.01); *C08K 3/26* (2013.01); *C08L 23/0861* (2013.01); *C08L 23/22* (2013.01); *C08L 23/283* (2013.01); *C08L 29/04* (2013.01); *C08L 53/02* (2013.01); *C08L 2201/14* (2013.01); *C08L 2203/10* (2013.01); *C08L 2203/16* (2013.01)

(58) Field of Classification Search
CPC .................................. C08L 23/22; C08L 29/04
See application file for complete search history.

(56) References Cited

U.S. PATENT DOCUMENTS

| | | |
|---|---|---|
| 4,299,759 A | 11/1981 | Miyata et al. |
| 5,895,797 A | 4/1999 | Hayashihara et al. |
| 6,028,147 A | 2/2000 | Ogawa et al. |
| 6,281,270 B1* | 8/2001 | Ito ................ B41M 5/5218 523/161 |
| 2003/0100647 A1* | 5/2003 | Parekh ................ C08K 9/04 524/394 |
| 2006/0167156 A1 | 7/2006 | Fukuda et al. |
| 2012/0225990 A1 | 9/2012 | Jacob |
| 2016/0137825 A1* | 5/2016 | Jakuczek ............. C08L 23/22 422/23 |
| 2017/0051158 A1* | 2/2017 | Hintze-Bruening ..... C08K 3/22 |

FOREIGN PATENT DOCUMENTS

| | | |
|---|---|---|
| EP | 0 905 156 A1 | 3/1999 |
| EP | 1 548 068 A1 | 6/2005 |
| EP | 2 634 215 A1 | 9/2013 |
| JP | 10-110086 A | 4/1998 |
| JP | 10-237299 A | 9/1998 |
| JP | 11-100420 A | 4/1999 |
| JP | 2000-157627 A | 6/2000 |
| JP | 2004-203922 A | 7/2004 |
| JP | 2006-131774 A | 5/2006 |
| WO | WO 2004/024825 A1 | 3/2004 |

OTHER PUBLICATIONS

International Search Report dated Dec. 6, 2016 in PCT/JP2016/082682 filed Nov. 2, 2016.
Extended European Search Report dated Jun. 6, 2019, in patent Application No. 16862163.9, 8 pages.

* cited by examiner

*Primary Examiner* — Jeffrey C Mullis
(74) *Attorney, Agent, or Firm* — Oblon, McClelland, Maier & Neustadt, L.L.P.

(57) ABSTRACT

Provided is a resin composition, comprising: an isobutylene-based copolymer (A) containing a halogen atom; an ethylene-vinyl alcohol copolymer (B); and a halogen scavenger (C), wherein a mass ratio (B/A) of the ethylene-vinyl alcohol copolymer (B) to the isobutylene-based copolymer (A) containing a halogen atom is from 20/80 to 50/50, and a content of the halogen scavenger (C) is from 0.01 to 1 part by mass based on 100 parts by mass of a total of the isobutylene-based copolymer (A) containing a halogen atom and the ethylene-vinyl alcohol copolymer (B). Such a resin composition is excellent in gas barrier properties and flexibility and stably produced over a long period of time.

10 Claims, No Drawings

RESIN COMPOSITION CONTAINING ISOBUTYLENE-BASED COPOLYMER, AND MOLDED OBJECT

TECHNICAL FIELD

The present invention relates to a resin composition containing an isobutylene-based copolymer and a shaped article thereof.

BACKGROUND ART

Materials having gas barrier properties and flexibility are required for: food packages in the form of a film, a sheet, a bag, a bottle, and the like; packings for a container to seal a beverage bottle with a bottle cap, seal a medical bottle with a lid, and the like; medical infusion solution bags; tire tubes; and the like.

For example, since a material for a food package requires flexibility and high gas barrier properties, laminates having a gas barrier layer containing an ethylene-vinyl alcohol-based copolymer or polyamide and a flexible resin layer are widely used. Since a material for a packing for a container requires flexibility and gas barrier properties, NR (natural rubber) and IIR (butyl rubber) are generally used. Since a material for a medical infusion solution bag requires flexibility and gas barrier properties, vinyl chloride is generally used. Since a material for a tire tube requires flexibility and high gas barrier properties, IIR is generally used.

IIR, however, needs complex vulcanization after molding to exhibit flexibility in a shaped article using IIR while IIR is excellent in flexibility [durometer hardness (type A) of approximately 65] and gas barrier properties [OTR of approximately 4000 cc·20 μm/(m²·day·atm)]. Although being excellent in gas barrier properties, such an ethylene-vinyl alcohol-based copolymer and polyimide are insufficient in flexibility and thus a laminate of a barrier layer of such a resin and a flexible resin layer is used as a food package, and as a result, limitation and complexity are brought to molding process. Having not so high gas barrier properties, NR is disadvantageous in longer shelf life of the contents when used as a material for a packing for containers and the like. Shaped articles using vinyl chloride are concerned about harmful influence on the environment due to generation of hydrogen chloride gas during incineration disposal.

As polymer materials excellent in flexibility and not requiring vulcanization, thermoplastic elastomers, such as SEBS (styrene-ethylene butylene-styrene triblock copolymer) and SEPS (styrene-ethylene propylene-styrene triblock copolymer), are proposed. However, depending on the use, the gas barrier properties are sometimes insufficient.

In comparison, as a resin composition applicable to a food package, a packing for a container, a medical infusion solution bag, a tire tube, and the like, a resin composition is proposed containing a block copolymer having a polymer block comprising vinyl aromatic monomer units and a polymer block comprising isobutylene units and an ethylene-vinyl alcohol-based copolymer (refer to Patent Document 1). This polymer composition is described as excellent in flexibility and gas barrier properties. However, when the polymer composition described in Patent Document 1 is produced over a long period of time, the production becomes difficult due to cross-linking of the polymers, causing difficulty in stable production of the polymer composition.

PRIOR ART DOCUMENT

Patent Document

Patent Document 1: JP 10-110086 A

SUMMARY OF THE INVENTION

Problems to be Solved by the Invention

The present invention has been made to solve the above problems, and it is an object thereof to provide a resin composition that is excellent in flexibility and gas barrier properties and stably produced over a long period of time. It is also an object thereof to provide a shaped article using the resin composition.

Means for Solving the Problems

The above problems are solved by providing a resin composition, comprising: an isobutylene-based copolymer (A) containing a halogen atom; an ethylene-vinyl alcohol copolymer (B) (hereinafter, "ethylene-vinyl alcohol copolymer" may be referred to as "EVOH"); and a halogen scavenger (C), wherein a mass ratio (B/A) of the ethylene-vinyl alcohol copolymer (B) to the isobutylene-based copolymer (A) is from 20/80 to 50/50, and a content of the halogen scavenger (C) is from 0.01 to 1 part by mass based on 100 parts by mass of a total of the isobutylene-based copolymer (A) and the ethylene-vinyl alcohol copolymer (B).

In this context, it is preferred that the halogen scavenger (C) is a layered inorganic compound having an exchangeable ion, and it is more preferred that the layered inorganic compound is hydrotalcite. It is also preferred that the halogen atom contained in the isobutylene-based copolymer (A) is a chlorine atom. It is also preferred that the isobutylene-based copolymer (A) is a block copolymer having a polymer block (a1) comprising vinyl aromatic monomer units and a polymer block (a2) comprising isobutylene units.

It is preferred that the resin composition comprises from 0.001 to 0.2 part by mass of carboxylic acid metal salt (D) based on 100 parts by mass of a total of the isobutylene-based copolymer (A) and the ethylene-vinyl alcohol copolymer (B).

A preferred embodiment of the present invention is a shaped article comprising a layer of the resin composition. The shaped article is suitably used as a food package, a packing for a container, a medical infusion solution bag, and a tire tube.

Effects of the Invention

The resin composition of the present invention is excellent in flexibility and gas barrier properties and, even when produced over a long period of time, prevents cross-linking of the resin and is thus stably produced. Shaped articles using the resin composition are excellent in flexibility and gas barrier properties and moreover have a good appearance (appearance with less aggregates derived from the halogen scavenger).

MODES FOR CARRYING OUT THE INVENTION

The resin composition of the present invention comprises: an isobutylene-based copolymer (A) containing a halogen atom; an ethylene-vinyl alcohol copolymer (B); and a halogen scavenger (C), wherein a mass ratio (B/A) of the ethylene-vinyl alcohol copolymer (B) to the isobutylene-based copolymer (A) is from 20/80 to 50/50, and a content of the halogen scavenger (C) is from 0.01 to 1 part by mass based on 100 parts by mass of a total of the isobutylene-based copolymer (A) and the ethylene-vinyl alcohol copolymer (B).

The isobutylene-based copolymer (A) containing a halogen atom contained in the resin composition of the present invention may be a copolymer with an isobutylene unit content of 20 mass % or more, and other copolymerizable monomers are not particularly limited.

Among all, as the isobutylene-based copolymer (A), a block copolymer having a polymer block (a1) comprising vinyl aromatic monomer units and a polymer block (a2) comprising isobutylene units is preferred. By containing such a block copolymer, the flexibility of the resin composition is further improved. The block copolymer may have at least one polymer block (a1) and at least one polymer block (a2) in a molecule and its structure is not particularly limited. For example, the block copolymer may have any molecular chain formation of a linear chain, a branched chain branched into two or more chains, and a star chain. The block copolymer used as the isobutylene-based copolymer (A) is typically a diblock structure represented by a1-a2, a triblock structure represented by a1-a2-a1 or a2-a1-a2, a tetrablock structure represented by a1-a2-a1-a2, a polyblock structure in which a total of 5 or more a1 and a2 are linearly bonded, or a mixture thereof. One type of the isobutylene-based copolymer (A) may be used singly, or two or more types may also be used as a mixture.

The vinyl aromatic monomer units as a constitutional unit of the polymer block (a1) are units derived from a vinyl aromatic monomer by addition polymerization. As such a vinyl aromatic monomer, those containing no halogen atom are preferred from the perspective of inhibiting cross-linking during production over a long period of time, and examples of the monomer include a vinyl-group containing aromatic compound, such as styrenes, like styrene, α-methylstyrene, 2-methylstyrene, and 4-methylstyrene, and vinylnaphthalenes, like 1-vinylnaphthalene and 2-vinylnaphthalene, for example. Vinyl aromatic monomer units constituting the polymer block (a1) may be one or more types. Among them, the polymer block (a1) preferably comprises styrene units.

From the perspective of improvement in mechanical properties of a resin composition produced therefrom, the polymer block (a1) has a number average molecular weight with a lower limit of preferably 1000 and more preferably 2000. Meanwhile, the polymer block (a1) has a number average molecular weight with an upper limit of preferably 400000 and more preferably 200000. When the number average molecular weight of the polymer block (a1) is in the above range, melt viscosity of the isobutylene-based copolymer (A) does not become too high and the isobutylene-based copolymer is readily mixed with the EVOH (B) described later, and thus moldability and workability of a resin composition produced therefrom are improved.

In the block copolymer used as the isobutylene-based copolymer (A), the isobutylene units as a constitutional unit of the polymer block (a2) are units ($-C(CH_3)_2-CH_2-$) derived from isobutylene by addition polymerization. The polymer block (a2) preferably has a number average molecular weight with a lower limit of 10000. This causes a resin composition produced therefrom to have particularly good gas barrier properties. Meanwhile, the polymer block (a2) preferably has a number average molecular weight with an upper limit of 400000. When the number average molecular weight of the polymer block (a2) is in the above range, moldability and workability of a resin composition produced therefrom are improved.

The ratio of the polymer block (a1) to the polymer block (a2) contained in the block copolymer used as the isobutylene-based copolymer (A) may be appropriately determined, whereas the lower limit of the content of the polymer block (a1) in the block copolymer is preferably 5 mass %, more preferably 10 mass %, and even more preferably 15 mass % based on the total mass of the isobutylene-based copolymer (A). When the content of the polymer block (a1) is the lower limit or more, mechanical properties, such as strength, of a resin composition produced therefrom are improved. Meanwhile, the upper limit of the content of the polymer block (a1) is preferably 80 mass %, more preferably 70 mass %, and even more preferably 50 mass % based on the total mass of the isobutylene-based copolymer (A). When the content of the polymer block (a1) is the upper limit or less, melt viscosity does not become too high, and thus moldability and workability of a resin composition produced therefrom are improved. When a plurality of polymer blocks (a1) are contained in the isobutylene-based copolymer (A), a total amount of them is defined as the content of the polymer block (a1).

The isobutylene-based copolymer (A) contained in the resin composition of the present invention contains a halogen atom. The halogen atom is considered to be derived from a polymerization catalyst used for production of the isobutylene-based copolymer (A) and mainly contained in a terminal of the isobutylene-based copolymer (A). Examples of the halogen atom contained in the isobutylene-based copolymer (A) include chlorine, bromine, fluorine, iodine, and the like, and among all, chlorine is often contained. The halogen atom content in the isobutylene-based copolymer (A) is generally from 0.005 to 3.000 mass %. The halogen atoms in the isobutylene-based copolymer (A) can be analyzed using an ion chromatograph.

The isobutylene-based copolymer (A) has a number average molecular weight with a lower limit of preferably 12000 and more preferably 30000. When the number average molecular weight is the lower limit or more, mechanical properties, such as strength and degree of elongation, of a resin composition produced therefrom are improved. Meanwhile, the isobutylene-based copolymer (A) has a number average molecular weight with an upper limit of preferably 600000 and more preferably 400000. When the number average molecular weight of the isobutylene-based copolymer (A) is the upper limit or less, moldability and workability of a resin composition produced therefrom are improved.

The isobutylene-based copolymer (A) has a melt flow rate (measured by the method according to ASTM D1238 in the conditions at a temperature of 230° C. and under a load of 2160 g and, hereinafter, "melt flow rate" may be referred to as "MFR") with a lower limit of preferably 0.05 g/10 min., more preferably 2.5 g/10 min., and even more preferably 5.0 g/10 min. Meanwhile, the isobutylene-based copolymer (A) has an MFR with an upper limit of preferably 100 g/10 min., more preferably 50 g/10 min., and even more preferably 20 g/10 min. When the MFR is in the above range, moldability and workability of a resin composition produced therefrom are improved.

Further, a functional group may be introduced into the isobutylene-based copolymer (A) by an arbitrary method as long as the effects of the present invention are not impaired. Examples of the functional group that can be introduced include: a hydroxyl group; an amino group; an alkylamino group; ether groups, such as an epoxy group and an alkoxyl group; a carboxyl group; ester groups, such as an alkoxycarbonyl group and an acyloxyl group; amido groups, such as a carbamoyl group, an alkylcarbamoyl group, and an acylamino group; groups having a structure of dicarboxylic anhydride, such as a maleic anhydride residue; and the like.

A method of producing the isobutylene-based copolymer (A) is not particularly limited, but for production of a block copolymer, preferred production methods are those by performing polymerization operation of vinyl aromatic monomers and polymerization operation of isobutylene stepwise in an arbitrary order in an inert solvent using a polymerization initiator. A preferred polymerization initiator used in that case is a combination of Lewis acid and an organic compound capable of generating an activated species for cationic polymerization by the Lewis acid. As such Lewis acid, halogen atom containing compounds are used, such as titanium tetrachloride, tin tetrachloride, boron trichloride, and aluminum chloride. Use of such Lewis acid allows efficient production of the isobutylene-based copolymer (A). When such a halogen atom containing compound is used as the Lewis acid, it is known that the halogen atom is contained in a terminal of the isobutylene-based copolymer (A). As the organic compound capable of generating an activated species for cationic polymerization by the Lewis acid, for example, bis(1-methoxy-1-methylethyl)benzene, bis(1-acetoxy-1-methylethyl)benzene, bis(1-chloro-1-methylethyl)benzene, and the like may be used. As the inert solvent for polymerization, organic solvents, such as hexane, cyclohexane, methylcyclohexane, methyl chloride, and methylene chloride, may be used.

Further, as the method of producing the isobutylene-based copolymer (A), for example, a preferred method comprises adding isobutylene in a reaction system for polymerization using the Lewis acid and the organic compound having one, two, or three functional groups capable of generating an activated species for cationic polymerization in a molecule described above as a polymerization initiator to form the polymer block (a2), followed by polymerization of the vinyl aromatic monomers to form the polymer block (a1).

The EVOH (B) contained in the resin composition of the present invention is a copolymer comprising mainly containing ethylene units and vinyl alcohol units and is produced by saponifying vinyl ester units in an ethylene-vinyl ester copolymer. The EVOH (B) used in the present invention is not particularly limited and may be a known one used for melt molding. One type of the EVOH (B) may be used singly, or two or more types may also be used as a mixture.

The lower limit of the ethylene unit content in the EVOH (B) is preferably 20 mol % and more preferably 24 mol %. When the content is below the lower limit, there is a risk of reducing melt moldability of a resin composition produced therefrom. Meanwhile, the upper limit of the ethylene unit content in the EVOH (B) is preferably 65 mol %, more preferably 60 mol %, and even more preferably 48 mol %. When the content is more than the upper limit, there is a risk of reducing gas barrier properties of a resin composition produced therefrom.

From the perspective of maintaining the gas barrier properties of a resin composition produced therefrom, the EVOH (B) has a degree of saponification of, but not particularly limited to, preferably 90 mol % or more, more preferably 95 mol % or more, and even more preferably 99 mol % or more.

The EVOH (B) has an MFR (measured by the method according to ASTM D1238 in the conditions at a temperature of 210° C. and under a load of 2160 g) with a lower limit of preferably 0.5 g/10 min., more preferably 1.0 g/10 min., and even more preferably 2.0 g/10 min. Meanwhile, the MFR has an upper limit of preferably 100 g/10 min., more preferably 50 g/10 min., and even more preferably 25 g/10 min. When the MFR is in the above range, moldability and workability of a resin composition produced therefrom are improved.

The EVOH (B) may have other constitutional units in addition to the ethylene units, the vinyl alcohol units, and the vinyl ester units. Examples of such other constitutional units include units derived from a vinyl silane compound, such as vinyltrimethoxysilane, vinyltriethoxysilane, vinyl tri(β-methoxy-ethoxy)silane, and γ-methacryloxypropylmethoxysilane. Among them, units derived from vinyltrimethoxysilane or vinyltriethoxysilane are preferred. Further, the EVOH (B) may have units derived from, as long as the objects of the present invention are not impaired, olefins, such as propylene and butylene; unsaturated carboxylic acids and esters thereof, such as (meth)acrylic acid and methyl (meth)acrylate; and vinylpyrrolidones, such as N-vinylpyrrolidone. The content of the units other than the ethylene units, the vinyl alcohol units, and the vinyl ester units is preferably 10 mol % or less and more preferably 5 mol % or less based on the total constitutional units.

As a method of producing the EVOH (B), for example, an ethylene-vinyl ester copolymer is produced in accordance with a known method, followed by saponification to produce the EVOH (B). Such an ethylene-vinyl ester copolymer is produced by polymerizing, for example, ethylene and vinyl ester using a radical polymerization initiator, such as benzoyl peroxide and azobisisobutyronitrile, under pressure in an organic solvent, such as methanol, t-butyl alcohol, and dimethyl sulfoxide. For vinyl ester as a raw material, vinyl acetate, vinyl propionate, vinyl pivalate, and the like may be used, and among them, vinyl acetate is preferred. For saponification of the ethylene-vinyl ester copolymer, an acid catalyst or an alkaline catalyst can be used.

In the resin composition of the present invention, a mass ratio (B/A) of the EVOH (B) to the isobutylene-based copolymer (A) has to have a lower limit of 20/80, preferably 25/75, and more preferably 30/70. When the mass ratio (B/A) is less than the lower limit, the gas barrier properties of the resin composition are reduced. Meanwhile, the mass ratio (B/A) has to have an upper limit of 50/50, preferably 45/55, and more preferably 40/60. When the mass ratio (B/A) is more than the upper limit, the flexibility of the resin composition is insufficient.

The halogen scavenger (C) contained in the resin composition of the present invention may have halogen trapping ability, and examples of the halogen scavenger include: a layered inorganic compound having an exchangeable ion; alkaline earth metal compounds, such as magnesium oxide, calcium hydroxide, magnesium hydroxide, and calcium carbonate; zinc oxide; lithium carbonate; and the like.

Among all, the halogen scavenger (C) is preferably a layered inorganic compound having an exchangeable ion. An ion between layers in the layered inorganic compound is exchanged for a halogen ion, and the halogen ion is thus incorporated into the layered inorganic compound. Examples of the layered inorganic compound include: clay mineral; layered polysilicate; layered silicate; layered double hydroxide; layered phosphate; layered transition metal oxysalts, such as titanium niobate, hexaniobate, and molybdate; layered manganate; layered cobalt oxide; and the like, and among all, clay mineral is preferred.

Examples of the clay mineral include hydrotalcite, zeolite, mica, vermiculite, montmorillonite, beidellite, saponite, hectorite, and stevensite. The clay mineral may be synthetic clay or natural clay. Among all, as the clay mineral, hydrotalcite and zeolite are preferred and the former is more preferred. Respective examples of the hydrotalcite and the zeolite include those represented by general formulae (I) and (II) below.

$$Mg_{1-a}Al_a(OH)_2(CO_3)_{a/2} \cdot xH_2O \quad (I)$$

$$Na_2O \cdot Al_2O_3 \cdot 2SiO_2 \cdot yH_2O \quad (II)$$

(In the formulae I and II, x denotes a number from 0 to 5, a denotes a number satisfying $0 < a \leq 0.5$, and y denotes a number from 0 to 6.)

In the resin composition of the present invention, the content of the halogen scavenger (C) has to have a lower limit of 0.01 part by mass and preferably 0.025 part by mass based on 100 parts by mass of a total of the isobutylene-based copolymer (A) and the EVOH (B). When the content of the halogen scavenger (C) is less than the lower limit, the resin rapidly cross-links during production of the resin composition over a long period of time. Meanwhile, the content of the halogen scavenger (C) has to have an upper limit of 1 part by mass and preferably 0.8 part by mass based on 100 parts by mass of a total of the isobutylene-based copolymer (A) and the EVOH (B). When the content of the halogen scavenger (C) is more than the upper limit, the number of aggregates derived from the halogen scavenger increases in a shaped article produced therefrom and the appearance is impaired.

In the resin composition of the present invention, a mass ratio [(C)/halogen atoms] of the halogen scavenger (C) to the halogen atoms contained in the isobutylene-based copolymer (A) is preferably 0.10 or more, more preferably 0.15 or more, even more preferably 0.20 or more, and particularly preferably 0.25 or more. The mass ratio [(C)/halogen atoms] is preferably 10 or less, more preferably 2 or less, and even more preferably 1 or less. The mass ratio [(C)/halogen atoms] in the above range allows more inhibition of development of the cross-linking during long term production and aggregation of the halogen scavenger and suppresses excessive use of the halogen scavenger (C), thereby enabling cost reduction.

Containing the halogen scavenger (C) described above is a major characteristic of the resin composition of the present invention. As a result of investigation on the cause of the rapid cross-linking reaction during melt kneading of the isobutylene-based copolymer (A) and the EVOH (B), the present inventors have found that the cause was the halogen atom contained in the isobutylene-based copolymer (A). It is considered that, when a resin composition is produced by melt kneading the isobutylene-based copolymer (A) and the EVOH (B), the halogen atoms in the isobutylene-based copolymer (A) are eliminated to by-produce hydrogen halide and the like and such a by-product accelerates the cross-linking reaction between the isobutylene-based copolymer (A) and the EVOH (B). The present inventors have then found that the cross-linking between the isobutylene-based copolymer (A) and the EVOH (B) is inhibited without increasing aggregates derived from the halogen scavenger by containing a predetermined amount of the halogen scavenger (C). Conventionally, addition of a halogen scavenger to an EVOH has been considered to increase aggregates derived from the halogen scavenger and impair the appearance of a shaped article produced therefrom, and thus a halogen scavenger has not been added to a composition containing an EVOH. The effects of the halogen scavenger (C) as described above were first found as a result of the investigation by the present inventors. The cross-link inhibiting effect of the present invention not only inhibits gelation generated in a short time but also inhibits development of cross-linking reaction during production over a long period of time.

In the resin composition of the present invention, a total amount of the isobutylene-based copolymer (A), the EVOH (B), and the halogen scavenger (C) is preferably 50 mass % or more, more preferably 80 mass % or more, and even more preferably 95 mass % or more.

The resin composition of the present invention preferably further comprises from 0.001 to 0.3 part by mass of carboxylic acid metal salt (D) based on 100 parts by mass of a total of the isobutylene-based copolymer (A) and the EVOH (B). This allows further inhibition of rapid cross-linking between the isobutylene-based copolymer (A) and the EVOH (B) even when the halogen scavenger (C) is contained less in the resin composition. As carboxylic acid constituting the carboxylic acid metal salt (D), carboxylic acid having a carbon number of from 1 to 30 is preferred, and specific examples of the carboxylic acid include acetic acid, stearic acid, lauric acid, montanic acid, behenic acid, octylic acid, sebacic acid, ricinoleic acid, myristic acid, palmitic acid, and the like, and among all, acetic acid and stearic acid are particularly preferred. As metal constituting the carboxylic acid metal salt (D), alkaline earth metal is preferred, and specific examples of the metal include magnesium, calcium, and the like.

From the perspective of thermal stability and viscosity control, the resin composition of the present invention may contain compounds, such as metal salt and acid, other than the carboxylic acid metal salt (D). Such compounds are carboxylic acid, phosphate compounds, boron compounds, and the like, and specific examples of them include the followings. These compounds may be contained in the isobutylene-based copolymer (A) or the EVOH (B) in advance.

Carboxylic acid: oxalic acid, succinic acid, benzoic acid, citric acid, acetic acid, lactic acid, etc.

Phosphate compound: various types of acid, salt thereof, etc., such as phosphoric acid and phosphorous acid Boron compound: boric acids, borate ester, borate, boron hydrides, etc.

The resin composition may contain various types of additives other than above as long as the effects of the present invention are not impaired. Examples of such additives include an antioxidant, a plasticizer, an ultraviolet absorber, an antistatic agent, a lubricant, a colorant, a filler, a nucleating agent, a flame retardant, a polymer other than the isobutylene-based copolymer (A) and the EVOH (B), and the like. In the resin composition, the content of the components other than the isobutylene-based copolymer (A), the EVOH (B), and the halogen scavenger (C) is preferably 50 mass % or less, more preferably 20 mass % or less, and even more preferably 5 mass % or less.

Examples of the polymer other than the isobutylene-based copolymer (A) and the EVOH (B) contained in the resin composition include: rubber, such as EPR (ethylene-propylene based rubber), EPDM (ethylene-propylene-diene based rubber), NR (natural rubber), isoprene rubber, butadiene rubber, and IIR (butyl rubber); and thermoplastic resins, such as polyethylene, polypropylene, polybutene, polyisobutylene, polyamide, and polyester. The content of the polymer other than the isobutylene-based copolymer (A) and the EVOH (B) contained in the resin composition has an upper limit of preferably 20 mass %, more preferably 10 mass %, and even more preferably 5 mass % based on the total polymer components. Meanwhile, in the resin composition, the total amount of the isobutylene-based copolymer (A) and the EVOH (B) has a lower limit of preferably 80 mass %, more preferably 90 mass %, and even more preferably 95 mass % based on the total polymer components.

A method of preparing the resin composition of the present invention preferably includes, but not particularly limited to, adding the halogen scavenger (C) to the isobutylene-based copolymer (A) and the EVOH (B) and then melt kneading for preparation, and the method is performed using a known mixing apparatus or a known kneading apparatus, such as a kneader-rudder, an extruder, a mixing roll, and a Banbury mixer. The temperature during melt kneading is generally from 110 to 300° C. The halogen scavenger (C) may be contained in the isobutylene-based copolymer (A) or the EVOH (B) in advance.

<Shaped Article>

A shaped article of the present invention comprises the resin composition.

Since the resin composition of the present invention has thermoplasticity, it can be mold processed using a general mold processing method and a general mold processing apparatus used for general thermoplastic polymers. As the mold processing method, an arbitrary method may be employed, such as injection molding, extrusion molding, press molding, blow molding, calender molding, and vacuum molding, for example. The shaped article comprising the resin composition produced by such a method include those in a wide variety of shapes, such as a molded product, a pipe, a sheet, a film, a tube, a disk, a ring, a bag-like product, a bottle-like product, a string-like product, and a fibrous product. Preferred shapes of the shaped article include a film form and a tube form.

As the shaped article, a shaped article having a layer comprising the resin composition is preferred. The shaped article may be a single layer structure or may be a laminate as long as it has a layer comprising the resin composition. From the perspective of improvement in moisture resistance, mechanical properties, and the like, the shaped article is preferably a laminate having a layer comprising the resin composition.

The laminate has at least one layer comprising the resin composition and at least one layer comprising another material. Such another material may be appropriately selected by preference in accordance with the required properties, the intended use, and the like. Such another material is preferably a thermoplastic resin, and examples of such another material include: polyolefins, such as high density polyethylene, medium density polyethylene, low density polyethylene, linear low density polyethylene, an ethylene-propylene copolymer, and polypropylene; thermoplastic polymers, such as an ethylene-vinyl acetate copolymer, an ethylene-acrylic ester copolymer, polystyrene, a vinyl chloride resin, and a vinylidene chloride resin; ionomers; and the like. The thermoplastic resin may be the isobutylene-based copolymer (A) or the EVOH (B).

The laminate may have an adhesive layer or an adhesive interposed between the resin composition layer and the layer comprising another material. The interposed adhesive layer or adhesive allows firm bonding integration of the two layers on both sides. As the adhesive layer or the adhesive, a diene-based polymer modified with acid anhydride; polyolefin modified with acid anhydride; a mixture of polymer polyol and a polyisocyanate compound; and the like may be used, and particularly when the layer comprising another material is a polyolefin layer, the interlayer adhesion is excellent without interposing the adhesive layer or the adhesive and thus the interposed adhesive layer or adhesive has less significance. To form a multilayer structure, a known method, such as coextrusion, coinjection, and extrusion coating, may be used.

The shaped article of the present invention preferably has a thickness of from 50 to 5000 μm. When the shaped article is a laminate, the layer comprising the resin composition of the present invention preferably has a thickness of from 5 to 500 μm and the layer comprising another material preferably has a thickness of from 45 to 4500 μm.

The shaped article is excellent in gas barrier properties and flexibility in good balance, and is thus applicable as household goods, packaging materials, mechanical components, and the like requiring these properties. Examples of the use particularly effectively exhibiting the characteristics of the shaped article include a food package, a packing for a container, a medical infusion solution bag, a tire tube, a cushion for shoes, a container, an inner bag for a bag in box, an organic liquid storage tank, an organic liquid carrying pipe, a heating hot water pipe (hot water pipe for floor heating, etc.), and the like. Among them, particularly preferred uses include a food package, a packing for containers, a medical infusion solution bag, and a tire tube.

EXAMPLES

The present invention is more specifically described below with reference to Examples.

[Atomic Weight of Chlorine]

The isobutylene-based copolymer (A) was pretreated by a combustion and absorption apparatus ("AQF-2100H" manufactured by Mitsubishi Chemical Analytech Co., Ltd.). The atomic weight of chlorine was detected by measuring the treated liquid thus produced with an ion chromatograph ("ICS-2000" manufactured by Nippon Dionex K.K.).

[Isobutylene-Based Copolymer]

A-1 to A-3 are described later in Synthesis Examples 1 to 3.

A-4: "SIBSTAR 062T" produced by Kaneka Corp., styrene-isobutylene-styrene block copolymer MFR of 10 g/10 min. (230° C., load of 2160 g); styrene unit containing polymer block content of 24 mass % with a number average molecular weight of 60000; isobutylene unit containing polymer block content of 77 mass %; chlorine atom content of 0.11 mass %

A-5: "Taftec H1041" produced by Asahi Kasei Corp., styrene-ethylene butylene-styrene block copolymer MFR of 5.0 g/10 min.; styrene unit containing polymer block content of 30 mass %; butadiene unit containing polymer block content of 70 mass %; chlorine atom content of 0.00 mass %

[Ethylene Content and Degree of Saponification of EVOH]

They were obtained by $^1$H-NMR measurement using "JNM-GX-500" manufactured by JEOL Ltd. as a measuring device and DMSO-$d_6$ as a solvent.

[Melt Flow Rate (MFR)]

The MFR was obtained by measuring the exit velocity (g/10 min.) of a measurement sample by the method according to ASTM D1238 in predetermined conditions (isobutylene-based copolymer: at a temperature of 230° C. under a load of 2160 g; EVOH: at a temperature of 210° C. under a load of 2160 g) using a melt indexer ("A-111A" manufactured by Toyo Seiki Seisaku-sho, Ltd.).

[EVOH]

B-1: "EVAL F104B" produced by Kuraray Co. Ltd., EVOH

MFR of 10.0 g/10 min., ethylene content of 32 mol %, degree of saponification of 99.99 mol %

B-2: "EVAL L104B" produced by Kuraray Co. Ltd., EVOH MFR of 8.9 g/10 min., ethylene content of 27 mol %, degree of saponification of 99.99 mol %

B-3: "EVAL E105B" produced by Kuraray Co. Ltd., EVOH MFR of 13.0 g/10 min., ethylene content of 44 mol %, degree of saponification of 100.0 mol %

B-4: "Novatec LD LJ400" produced by Japan Polyethylene Corp., low density polyethylene MFR of 1.5 g/10 min. (190° C., load of 2160 g), density of 0.921 g/cm³

[Halogen Scavenger]

C-1: "ZHT-4A" produced by Kyowa Chemical Industry Co., Ltd., hydrotalcite

C-2: "DHT-4A" produced by Kyowa Chemical Industry Co., Ltd., hydrotalcite

[Carboxylic Acid Metal Salt]

D-1: magnesium acetate

D-2: magnesium stearate

D-3: calcium acetate

[Evaluation of Time Until Cross-linking of Resin Composition]

The resin composition was weighed 75 g and put into a roller mixer ("R100" manufactured by Toyo Seiki Seisaku-sho, Ltd.) to be stirred at 230° C. and 100 rpm for temporal observation of change in torque. The time when the torque starts varying up and down continuously by 1 N·m or more was measured.

[Measurement of Durometer Hardness]

In accordance with JIS K 6253-3, the durometer hardness was measured in a state where two injected pieces described later were overlaid with each other to have a thickness of 8 mm using a durometer (type A) manufactured by Shimadzu Corp.

[Oxygen Transmission Rate (OTR)]

A single layer film described later was humidity-controlled at 20° C./65% RH, followed by measurement of an oxygen transmission rate (OTR) in accordance with the method described in JIS K 7126 (equal pressure method) in the conditions of 20° C./65% RH using an oxygen transmission rate measurement system ("OX-Tran2/20" manufactured by Modern Controls, Inc., etc.).

[Hydrotalcite Aggregate]

Using a single layer film described later, an appearance was evaluated as follows.

A: the film surface was smooth and almost no hydrotalcite aggregates were found.

B: the film surface was partially rough and slight hydrotalcite aggregates were found.

C: the film surface was rough and many hydrotalcite aggregates were found.

Synthesis Example 1

[Production of Isobutylene-Based Copolymer A-1]

Into a nitrogen-purged reactor with a stirrer, a mixed solvent of 1060 parts by mass of methylene chloride and 920 parts by mass of methylcyclohexene and a polymerization initiator of 2.7 parts by mass of titanium tetrachloride and 0.91 part by mass of 1,4-bis(1-methoxy-1-methylethyl)benzene were charged and cooled at −65° C., followed by charging of 150 parts by mass of isobutylene for polymerization for 4 hours. Further, in the cooling at −65° C., 0.08 parts by mass of dimethylacetamide and 38 parts by mass of styrene were added and polymerized for 4 hours. The reaction mixture thus produced was precipitated with methanol to produce an isobutylene-based copolymer B-1 (styrene-isobutylene-styrene triblock copolymer). The number average molecular weight of B-1 thus produced was obtained by GPC (gel permeation chromatography), and the number average molecular weight of each block in the block copolymer was obtained based on the GPC of polyisobutylene as a synthetic intermediate of the block copolymer, and the content of the styrene unit containing polymer block in the block copolymer was obtained by ¹H-NMR. These analysis results are shown in Table 1.

Synthesis Examples 2 and 3

[Production of Isobutylene-Based Copolymers A-2 and A-3]

Using the method same as Synthesis Example 1 except for changing the charge ratios of styrene, isobutylene, and 1,4-bis(1-methoxy-1-methylethyl)benzene, isobutylene-based copolymer A-2 and isobutylene-based copolymer A-3 (styrene-isobutylene-styrene triblock copolymers) were respectively produced. The results of analysis in the same manner as Synthesis Example 1 are shown in Table 1.

TABLE 1

| Synthesis Example | Number Average Molecular Weight of Isobutylene-Based Copolymer (A) | Number Average Molecular Weight of Polystyrene Block | Number Average Molecular Weight of Polyisobutylene Block | Polystyrene Block Content (mass %) | Chlorine Atom Content (mass %) |
|---|---|---|---|---|---|
| 1 | 25000 | 2500 | 20000 | 20 | 2.8 |
| 2 | 37000 | 5500 | 26000 | 30 | 1.9 |
| 3 | 65000 | 8000 | 49000 | 25 | 1.1 |

Example 1

[Production of Resin Composition]

A-1 was used as the isobutylene-based copolymer (A), B-1 was used as the EVOH (B), and C-1 was used as the halogen scavenger (C). First, A-1 (60 parts by mass) and B-1 (40 parts by mass) were dry blended, and to the mixture thus produced, C-1 (0.25 part by mass) was added and then melt kneaded, followed by pelletization and drying to obtain pellets of the resin composition. The results of evaluation of cross-linking properties of the resin composition thus produced by the above method are shown in Table 2. The melt kneading conditions are described below.

<Melt Kneading Conditions>

Apparatus: 26 mmϕ twin screw extruder ("LABO PLAS-TOMILL 4C150" manufactured by Toyo Seiki Seisaku-sho, Ltd.)

Screw: co-rotating, fully intermeshing type

Number of die holes: 2 holes (3 mmϕ)

Extrusion temperature: C1=200° C., C2 to C5=230° C., die=230° C.

Drying: hot air drying 80° C./6 hr

[Production of Injected Piece]

The resin composition thus produced was injection molded in the following conditions to produce injected pieces. The evaluation results of the durometer hardness of the injected pieces by the above method are shown in Table 2.

<Injection Conditions>

Apparatus: injection molding machine ("FS-80S 12AS" manufactured by Nissei Plastic Industrial Co., Ltd.)

Cylinder temperature: rear portion/middle portion/front portion/nozzle=200° C./220° C./220° C./200° C.

Mold temperature: 60° C.

Mold: 80 mm×10 mm×4 mm×4 pieces
[Production of Single Layer Film]

The resin composition thus produced was formed into a film in the following conditions to produce a single layer film having a thickness of 100 μm. The evaluation results of the oxygen transmission rate and the hydrotalcite aggregates of the single layer film by the above method are shown in Table 2. The film formation conditions are described below.
<Film Formation Conditions>

Apparatus: 20 mmϕ twin single extruder ("LABO PLAS-TOMILL 4M150" manufactured by Toyo Seiki Seisaku-sho, Ltd.)
L/D: 20
Screw: full flight
Die: 300 mm coat hanger die
Extrusion temperature: C1=180° C., C2 to C3=220° C., die=220° C.
Screen: 50/100/50
Cooling roll temperature: 40° C.

Examples 2 to 13

In the same manner as Example 1 except for changing the type and the amount of the isobutylene-based copolymer (A), the EVOH (B), and the halogen scavenger (C) as shown in Table 2, each resin composition was produced and evaluated. Using the resin composition thus produced, injected pieces and a single layer film were produced and evaluated in the same manner as Example 1. The evaluation results for each are shown in Table 2.

Examples 14 to 17

In the same manner as Example 1 except for changing the amount of the halogen scavenger (C) as shown in Table 2 and further adding D-1, D-2, or D-3 in the respective amounts shown in Table 2 as the carboxylic acid metal salt (D) while melt kneading the isobutylene-based copolymer (A) and the EVOH (B), each resin composition was produced and evaluated. Using the resin composition thus produced, injected pieces and a single layer film were produced and evaluated in the same manner as Example 1. The evaluation results for each are shown in Table 2.

Comparative Example 1

In the same manner as Example 1 except for not adding the halogen scavenger (C), a resin composition was produced and evaluated. Using the resin composition thus produced, injected pieces and a single layer film were produced and evaluated in the same manner as Example 1. The evaluation results are shown in Table 2.

Comparative Examples 2 to 4

In the same manner as Example 1 except for changing the amount of the isobutylene-based copolymer (A), the EVOH (B), and the halogen scavenger (C) as shown in Table 2, each resin composition was produced and evaluated. Using the resin composition thus produced, injected pieces and a single layer film were produced and evaluated in the same manner as Example 1. The evaluation results for each are shown in Table 2.

Comparative Example 5

In the same manner as Example 2 except for using B-4 as low density polyethylene instead of the EVOH (B), a resin composition was produced and evaluated. Using the resin composition thus produced, injected pieces and a single layer film were produced and evaluated in the same manner as Example 1. The evaluation results are shown in Table 2.

Comparative Example 6

In the same manner as Example 2 except for using A-5 as a styrene-ethylene butylene-styrene block copolymer instead of the isobutylene-based copolymer (A), a resin composition was produced and evaluated. Using the resin composition thus produced, injected pieces and a single layer film were produced and evaluated in the same manner as Example 1. The evaluation results are shown in Table 2.

TABLE 2

|  | Example 1 | Example 2 | Example 3 | Example 4 | Example 5 | Example 6 | Example 7 | Example 8 | Example 9 |
|---|---|---|---|---|---|---|---|---|---|
| Isobutylene-Based Copolymer (A) (parts by mass) | A-1 60 | A-1 60 | A-1 60 | A-1 60 | A-1 60 | A-1 80 | A-1 50 | A-2 60 | A-3 60 |
| Chlorine Atom (mass %)[1] | 2.8 | 2.8 | 2.8 | 2.8 | 2.8 | 2.8 | 2.8 | 1.9 | 1.1 |
| EVOH (B) (parts by mass) | B-1 40 | B-1 40 | B-1 40 | B-1 40 | B-1 40 | B-1 20 | B-1 50 | B-1 40 | B-1 40 |
| Halogen Scavenger (C) (parts by mass) | C-1 0.25 | C-1 0.5 | C-1 0.1 | C-1 1 | C-1 0.01 | C-1 0.5 | C-1 0.5 | C-1 0.5 | C-1 0.5 |
| Carboxylic Acid Metal Salt (D) (parts by mass) | — 0 | — 0 | — 0 | — 0 | — 0 | — 0 | — 0 | — 0 | — 0 |
| Scavenger (C)/ Chlorine Atoms[2] | 0.15 | 0.30 | 0.06 | 0.60 | 0.01 | 0.22 | 0.36 | 0.44 | 0.76 |
| Evaluation of Time until Cross-Linking (min.) | 15 | 46 | 12 | 72 | 10 | 120 | 32 | 68 | 102 |
| Evaluation of Durometer Hardness (Type A) | 70 | 73 | 73 | 72 | 71 | 60 | 80 | 76 | 74 |
| Evaluation of Oxygen Transmission Rate [cc · 20 μm/m² · day · atm] | 1300 | 1200 | 1200 | 1300 | 1300 | 1800 | 700 | 1100 | 1200 |
| Evaluation of Hydrotalcite Aggregates | A | A | A | B | A | A | A | A | A |

TABLE 2-continued

|  | Example 10 | Example 11 | Example 12 | Example 13 | Example 14 | Example 15 | Example 16 | Example 17 | Comparative Example 1 |
|---|---|---|---|---|---|---|---|---|---|
| Isobutylene-Based Copolymer (A) (parts by mass) | A-4 60 | A-1 60 | A-1 60 | A-1 60 | A-1 60 | A-1 60 | A-1 60 | A-1 60 | A-1 60 |
| Chlorine Atom (mass %)[1] | 0.11 | 2.8 | 2.8 | 2.8 | 2.8 | 2.8 | 2.8 | 2.8 | 2.8 |
| EVOH (B) (parts by mass) | B-1 40 | B-2 40 | B-3 40 | B-1 40 | B-1 40 | B-1 40 | B-1 40 | B-1 40 | B-1 40 |
| Halogen Scavenger (C) (parts by mass) | C-1 0.5 | C-1 0.5 | C-1 0.5 | C-2 0.5 | C-1 0.5 | C-1 0.5 | C-1 0.5 | C-1 0.5 | — 0 |
| Carboxylic Acid Metal Salt (D) (parts by mass) | — 0 | — 0 | — 0 | — 0 | D-1 0.0352 | D-2 0.146 | D-3 0.0237 | D-1 0.3 | — 0 |
| Scavenger (C)/ Chlorine Atoms[2] | 7.58 | 0.30 | 0.30 | 0.30 | 0.30 | 0.30 | 0.30 | 0.30 | — |
| Evaluation of Time until Cross-Linking (min.) | 98 | 40 | 45 | 43 | 54 | 56 | 50 | 74 | 5 |
| Evaluation of Durometer Hardness (Type A) | 72 | 75 | 68 | 71 | 69 | 71 | 70 | 69 | 71 |
| Evaluation of Oxygen Transmission Rate [cc · 20 μm/m² · day · atm] | 1000 | 1100 | 1200 | 1200 | 1200 | 1200 | 1200 | 1200 | 1300 |
| Evaluation of Hydrotalcite Aggregates | A | A | A | A | A | A | A | A | A |

|  | Comparative Example 2 | Comparative Example 3 | Comparative Example 4 | Comparative Example 5 | Comparative Example 6 |
|---|---|---|---|---|---|
| Isobutylene-Based Copolymer (A) (parts by mass) | A-1 60 | A-1 90 | A-1 40 | A-1 60 | A-5 60 |
| Chlorine Atom (mass %)[1] | 2.8 | 2.8 | 2.8 | 2.8 | 0 |
| EVOH (B) (parts by mass) | B-1 40 | B-1 10 | B-1 60 | B-4 40 | B-1 40 |
| Halogen Scavenger (C) (parts by mass) | C-1 2.0 | C-1 0.5 | C-1 0.5 | C-1 0.5 | C-1 0.5 |
| Carboxylic Acid Metal Salt (D) (parts by mass) | — 0 | — 0 | — 0 | — 0 | — 0 |
| Scavenger (C)/ Chlorine Atoms[2] | 1.19 | 0.20 | 0.45 | 0.30 | — |
| Evaluation of Time until Cross-Linking (min.) | 83 | Not Cross-Linked | 60 | Not Cross-Linked | Not cross-linked |
| Evaluation of Durometer Hardness (Type A) | 72 | 52 | 87 | 68 | Not Moldable |
| Evaluation of Oxygen Transmission Rate [cc · 20 μm/m² · day · atm] | 1200 | 3000 | 30 | 3500 | Not Available for Film Formation |
| Evaluation of Hydrotalcite Aggregates | C | A | A | A | Not Available for Film Formation |

[1] Chlorine atom content in the isobutylene-based copolymer (A)
[2] Mass ratio in the resin composition of halogen scavenger (C) to chlorine atoms contained in the isobutylene-based copolymer (A)

In the resin compositions of the present invention (Examples 1 to 17), rapid torque variation was not observed even when they were melt kneaded over a long period of time, and the cross-linking of the resin was inhibited. The injected pieces produced by molding these resin compositions were excellent in flexibility. Further, the films produced by molding these resin compositions were excellent in gas barrier properties and had a good appearance with less aggregates derived from the halogen scavenger. In contrast, in the resin composition not containing the halogen scavenger (C) (Comparative Example 1), rapid cross-linking of the resin was affirmed from the torque variation in a short time during melt kneading. The film produced by molding the resin composition with the halogen scavenger (C) content of more than 1 part by mass (Comparative Example 2) had a poor appearance with many aggregates derived from the halogen scavenger. The film produced by molding the resin composition with the mass ratio (B/A) of the EVOH (B) to the isobutylene-based copolymer (A) of less than 20/80 (Comparative Example 3) was insufficient in the gas barrier properties. The injected pieces produced by molding the resin composition with the mass ratio (B/A) of the EVOH (B) to the isobutylene-based copolymer (A) of more than 50/50 (Comparative Example 4) were insufficient in the flexibility. The resin composition using low density polyethylene instead of the EVOH (B) (Comparative Example 5) was insufficient in the gas barrier properties. With the resin composition using the resin not containing a chlorine atom (Comparative Example 6), it was not possible to form injected pieces and a film and evaluation was not able to be made.

The invention claimed is:

1. A resin composition, comprising:
   (A) an isobutylene-based copolymer (A) containing a halogen atom;
   (B) an ethylene-vinyl alcohol copolymer (B);
   (C) a halogen scavenger (C);
   (D) an acetic acid metal salt (D),
   wherein:
   a mass ratio (B/A) of the ethylene-vinyl alcohol copolymer (B) to the isobutylene-based copolymer (A) is from 20/80 to 50/50;
   a content of the halogen scavenger (C) is from 0.01 to 1 part by mass based on 100 parts by mass of a total of the isobutylene-based copolymer (A) and the ethylene-vinyl alcohol copolymer (B); and
   a content of the acetic acid metal salt (D) is from 0.001 to 0.3 part by mass based on 100 parts by mass of a total of the isobutylene-based copolymer (A) and the ethylene-vinyl alcohol copolymer (B).

2. The resin composition according to claim 1, wherein the halogen scavenger (C) is a layered inorganic compound having an exchangeable ion.

3. The resin composition according to claim 2, wherein the layered inorganic compound is hydrotalcite.

4. The resin composition according to claim 1, wherein the halogen atom contained in the isobutylene-based copolymer (A) is a chlorine atom.

5. The resin composition according to claim 1, wherein the isobutylene-based copolymer (A) is a block copolymer having a polymer block (a1) comprising vinyl aromatic monomer units and a polymer block (a2) comprising isobutylene units.

6. A shaped article, comprising a layer of the resin composition according to claim 1.

7. The shaped article according to claim 6, wherein the shaped article is a food package.

8. The shaped article according to claim 6, wherein the shaped article is a packing for a container.

9. The shaped article according to claim 6, wherein the shaped article is a medical infusion solution bag.

10. The shaped article according to claim 6, wherein the shaped article is a tire tube.

* * * * *